United States Patent [19]
Bogdanski et al.

[11] Patent Number: 6,083,854
[45] Date of Patent: Jul. 4, 2000

[54] WET WIPES WITH LOW VISCOSITY SILICONE EMULSION SYSTEMS

[75] Inventors: Michael Scott Bogdanski, Bonn; Ursula Christina Glaser, Mainz, both of Germany

[73] Assignee: The Procter & Gamble Company, Cincinnati, Ohio

[21] Appl. No.: 09/029,461

[22] PCT Filed: Aug. 30, 1996

[86] PCT No.: PCT/US96/13987

§ 371 Date: Oct. 2, 1998

§ 102(e) Date: Oct. 2, 1998

[87] PCT Pub. No.: WO97/10100

PCT Pub. Date: Mar. 20, 1997

[30] Foreign Application Priority Data

Sep. 15, 1995 [EP] European Pat. Off. .............. 95114587

[51] Int. Cl.$^7$ ................................... B32B 30/72
[52] U.S. Cl. .......................... 442/157; 442/161; 442/162; 442/163
[58] Field of Search ..................... 442/157, 161, 442/162, 163

[56] References Cited

U.S. PATENT DOCUMENTS

| | | | |
|---|---|---|---|
| 4,904,524 | 2/1990 | Yoh ....................................... | 428/311.3 |
| 5,043,155 | 8/1991 | Puchalski et al. .................... | 514/772.5 |
| 5,525,346 | 6/1996 | Hartung et al. ........................ | 424/402 |
| 5,559,149 | 9/1996 | Clum et al. ............................. | 514/529 |
| 5,580,566 | 12/1996 | Syverson et al. ....................... | 424/404 |
| 5,763,332 | 6/1998 | Gordon et al. ........................... | 442/84 |
| 5,973,068 | 10/1999 | Yamaya et al. ......................... | 524/865 |

FOREIGN PATENT DOCUMENTS 0 763 341  3/1997  Germany ....................... A47L 13/17

Primary Examiner—Blaine Copenheaver
Assistant Examiner—Arti R. Singh
Attorney, Agent, or Firm—Judy A. Glaze; T. David Reed; Donald E. Hasse

[57] ABSTRACT

The present invention relates in general to a variety of emulsion compositions, and more particularly, to emulsion compositions and methods for preparing these emulsion compositions which employ novel polymeric emulsifaction techniques. The emulsion compositions of this invention although applicable to a variety of applications provide particularly stable low viscosity polymeric emulsions useful for example in connection with wet wipes for the treatment of adult or baby dermatitis, make-up removal and other skin care applications. The stabilizing composition used in the emulsions according to the present invention comprise phenoxyethanol.

11 Claims, No Drawings

WET WIPES WITH LOW VISCOSITY SILICONE EMULSION SYSTEMS

FIELD OF THE INVENTION

The present invention relates in general to a variety of emulsion compositions, and more particularly, to emulsion compositions and methods for preparing these emulsion compositions which employ novel polymeric emulsification techniques. The emulsion compositions of this invention although applicable to a variety of applications provide particularly stable low viscosity polymeric emulsions useful for example in connection with wet wipes for the treatment of adult or baby diaper dermatitis, make-up removal and other skin care applications.

BACKGROUND

Skin problems including diaper dermatitis are believed to be caused by the prolonged contact of the skin with skin active environmental factors including ammonia, UV-light, moisture, bacteria, urine, non-neutral pH, and others. Because these various suspected factors have different properties and require different approaches, the most effective method of treating skin has been the application of a topical protective barrier agent between the skin and the skin active environmental factors.

A detailed disclosure of topically applied barrier agents is disclosed in EP-A-328 355 which relates in general to wet wipes comprising low viscosity emulsion systems.

Baby wet wipes are premoistened, disposable towelettes used primarily during diaper changes for cleansing. The wipe is typically constructed of combinations of synthetic (e.g. polyolefin) fibers, viscose fibers, cotton fibers, and cellulose fibers. It is possible to also produce wipes from other synthetic or natural fibers not mentioned. Wipes are generally moistened with water and contain various combinations of emulsion systems, cleaning, surfactants, preservatives and scents. A detailed disclosure of baby wet wipes and ingredients they contain is also contained in EP-A-328 355.

In order to provide cleaning and skin treatment the combination of wipes and a protective barrier agent is typically used. The wipes are used initially, for cleansing, and than a barrier agent is applied for skin protection. Baby wipes currently available do not leave substantive or wash resistant residues to protect the skin, so called barrier agents, after application. Barrier agents are generally greasy and unappealing and are not effective cleansing agents. In addition, the used of some barrier agents may actually promote excessive skin hydration which may result in increased skin fraction.

There is thus a need in the treatment of skin for a hybrid product which would effectively cleanse and also leave a substantive protection residue on the skin. It would also be desirable to be able to apply the hybrid product premoistened as a wipe. The protective residue further should not significantly reduce transepidermal moisture loss.

EP-A-85 334 describes an oil in water composition comprising 40–95% water and 0.01–5% of an emulsifier. It is concerned with the formation of dermatologically acceptance of substantive topical oil in water emulsions which are useful for sunscreen composition applications. The document discloses composition incorporating a polyanhydride resin derived from a octadence-1 and maleic anhydride. The document is not concerned with forming a stable emulsion according to the present invention.

EP-A-268 164 is concerned with emulsions which contain a modified copolymer of a preponderant amount of an acrylic acid and a smaller amount of a long chain acrylate monomer. The emulsifier are stated to be stable over a period of over one year at room temperature but exhibit quick breaking properties when in contact with an electrolyte or the skin, instantaneously coalescing and releasing the oil. The use of highly cross linked polyacrylic acids in the formation of the emulsion is disclosed but not desirable in the context of wet-wipe applications which comprise electrolytes such as surfactants and preservatives/stabilisers.

EP-A-328 355 is concerned with oil-in-water emulsions which contain silicones and amphipathic emulsifying agents. Concentrate emulsions are formed using high shear forces, and then diluted with water to obtain the final emulsion. The emulsions are said to have viscosities of less than 100 mpas.

The present invention relates to wet-wipes with silicone-phase-in-water emulsions providing a medium to low viscosity for good cleaning, a polymeric emulsion system to reduce surfactant residue on the skin and a micorbial stabiliser providing storage stability. The present invention provides hence an alternative/a selection to the emulsions disclosed in EP-A-328 355.

DESCRIPTION OF THE INVENTION

According to the present invention wet wipes are provided with an emulsion composition comprising a silicone base phase in the range of 1% to 20%, preferably 2% to 10%, by weight of the composition. The emulsion composition further comprises a polymeric emulsifying agent in the range of 0.02% to 2.0%, preferably 0.1% to 1%, by weight of the composition, and a stability composition comprising phenoxyethanol as stability compound. In order for the emulsion to provide the wet wipe with good cleaning performance the delivered viscosity should be less than 500 mPas, preferably in the range of 300 to more than 100 mPas and most preferably in the range of 180 to 120 mPas.

The term "delivered viscosity" according to the present invention refers to the emulsifying composition as a liquid. In order to measure delivered viscosity it is necessary to measure the viscosity of a sample of the emulsifying composition after undergoing a test storage profile. According to the test storage profile the emulsion is stored for 30 days undergoing a daily temperature profile of 12 hours at 0° C. and 12 hours at 40° C. Obviously any actual storage conditions of wet wipes differ greatly from the test storage profile for delivered viscosity measurement but it has been found that this profile provides a stress condition assessment of the emulsion stability in terms of separating of the hydrophilic and hydrophobic compound. Therefore an emulsion which does not separate during a test according to the test storage profile satisfies the objectives of the present invention.

The different test is used to assess storage stability in respect to the microbial activity of a sample of the emulsion on a wet wipe. A sample of the wet wipe is inocculated with various strains of bacteria, yeasts and molds. After 6 weeks at elevated temperatures (about 45° C.) and one interim reinocculation after about 4 weeks the samples are considered by a microbiologists. If the inocculated microbes are under control, preferably if they are eliminated, then the storage stability in respect to microbial activity is considered satisfactory.

As is well known in the art wet wipes must not be contaminated with microbes. The test for microbial stability is hence to assess whether or not a wet wipe with an emulsion sample is safe for consumer use.

Preferably, the phenoxyethanol is present in the range of from 0.1 to 1.0% while the total quantity of stability composition should be in the range of 0.1% of 4% by weight of the emulsion composition.

In another preferred embodiment according to the present invention the stability composition comprises one or more of the following stability compounds, sodium benzoate, potassium sorbate, methylparaben, propylparaben, ethylparaben, butylparaben, and disodium salt ethylenediomine tetraocedic acid (hereinafter referred to as EDTA).

Advantageously, the silicone based phase is selected from the group consisting of dimethicone, cyclomethicone and dimethiconol, dimethicone and trimethylsiloxysilicate, cetyl dimethicone, or combinations thereof.

In a preferred embodiment the emulsifying agent is a copolymer of C10–C30 alkyl acrylates and one or more monomers of acrylic acid, methylacrylic acid or one of their simple esters cross linked with an allyl ether of sucrose or an allyl ether of pentaerythritol.

It is also in the interest of the present invention that a perfume is present.

In another aspect, the invention relates to the use of an emulsion composition of the type as described above in the manufacture of a premoistened towelette or wet wipe for the prophylaxis or treatment of diaper dermatitis.

The invention provides the basis for the formulation of a great variety of emulsion compositions for wet wipes, which cleanse and also leave a highly protective substantive residue on the skin. Such compositions are useful in a great variety of use, for example, in the treatment of adult or baby diaper dermatitis.

The emulsifying agents which may be used in the present invention are capable of primary emulsification of silicone-phase-in-water emulsions. The emulsifiers should be capable of rapidly inverting or de-emulsifying the emulsion to form an oil film upon application.

For a better understanding of the invention, embodiments of it will now be further described by way of example.

The silicone based phase materials (emollients or barrier aids) which are useful in the present invention are all silicone based and include dimethicone (Dow Corning 200 Fluids), cyclomethicone and dimethiconol (Dow Corning 1401 Fluid), cetyl dimethicone (Dow Corning 2502 Fluid), dimethicone and trimethylsiloxysilicate (Dow Corning 593 Fluid), cyclomethicone (Dow Corning 244, 245, 344 or 345 Fluid), phenyl trimethicone (Dow Corning 556 Fluid), or combinations thereof.

The emulsifying agents which are useful in the present invention include Pemulen TR1 and TR2 which are available from B.F. Goodrich company of the USA. Chemically they are a copolymers of C10–C30 alkyl acrylates and one or more monomers of acrylic acid, methylacrylic acid or one of their simple esters cross linked with an allyl ether of sucrose or an allyl ether of pentaerythritol.). Other useful emulsifying agents include those disclosed in detail in EP-A-328 355.

The stability composition according to the present invention addresses the need for microbial stability. Conventionally microbial stability compositions have sometimes regulatory or real consumer acceptance problems, as is well known for example for fomaldehyde in Europe. It hence was surprising to find that a generally acceptable compound, phenoxyethanol, preferably in a quantity of 0.1% to 1% by weight of the composition, can be used together with other stabilisers without adverse effects to separation stability of the emulsion composition. A preferred stability composition can comprise in addition to phenoxyethanol one or more of methylparaben, propylparaben, ethylparaben, butylparaben, sodium benzoate, potassium sorbate, and disodium EDTA or other EDTA salts (sequestrenes). Sequestrene is a series of complexing agents and metal complexes general of ethylenediaminetetraacetic acid and salts. The quantity of the stability composition should be as little as possible since it's function is only the prevention of microbial activity, a total quantity of from 0.1% to 4% has typically been found sufficient.

A brief description of the processes which can be used to produce the emulsion of the present invention follows. The emulsifying agent is dispersed into either the water or the silicone based phase. A neutralizing agent (base) is added to the water. When the emulsifying agent combines with the water and neutralizer, a polymeric gel is formed, which is capable of emulsifying the silicone into the water. Other ingredients may be added during the emulsification process, or thereafter. The process can be carried out using blade mixers or homogenizers of various well known types to blend the components, prior to impregnation of the wet wipe. The process does typically not require heating.

Optional ingredients which may be used in the present invention include preservatives, anti fungal agents, skin protectants, moisturizing/humectant agents, pH adjusters, powders, perfumes, and the like. A detailed description of such ingredients is given in EP-A-328 355 specifically referred to for identification of such substances.

The following EXAMPLE is one illustration of the emulsion composition according to the present invention:

A particularly preferred emulsion composition in the form of a barrier lotion useful for the treatment of diaper dermatitis was prepared in accordance with the present invention having the following composition:

| Trade Name | INCI Name | Parts by Weight | Actual Weight [g] |
| --- | --- | --- | --- |
| Pemulen TR2 | Acrylates/C10–C30 Alkyl Acrylate Crosspolymer | 0.200 | 3.00 |
| Dow Corning fluid DC 1401 | Cyclomethicone and Dimethiconol | 2.000 | 30.00 |
| Water, deionized | Water | 95.140 | 1427.10 |
| Triethanolamine | Triethanolamine | 0.110 | 1.65 |
| Sodium Benzoate | Sodium Benzoate | 0.400 | 6.00 |
| Trilon BD | Disodium EDTA | 0.100 | 1.50 |
| Propylene Glycol | Propylene Glycol | 1.010 | 15.15 |
| Methyl Paraben | Methyl Paraben | 0.200 | 3.00 |
| Propyl Paraben | Propyl Paraben | 0.040 | 0.60 |
| Phenoxyethanol | Phenoxyethanol | 0.700 | 10.50 |
| Fragrance | Fragrance | 0.100 | 1.50 |

The following process was used to produce the emulsion in this example:

Mixture A: Disperse Pemulen TR2 into the DC 1401 by using a Rotor/Stator homogenizer.

Mixture B: Mix 90 parts of the total water amount with Triethanolamine by using a blade type stirrer.

Mixture C: Disolve Sodium Benzoate and Trilon BD in the remaining 10 parts of the total water amount.

Mixture D: Disolve the Parabens in Propylene Glycol while stirring, then add Phenoxyethanol and fragrance.

Add mixture A to mixture B by using a blade type stirrer, keep on stirring this emulsion for 20 minutes.

Add mixture D to the emulsion, stirring with a blade type stirrer.

After 10 minutes of stirring add slowly mixture C, keep on stirring for 10 minutes.

This emulsion resulted in a viscosity of 126 mPas (as measured with a Brookfield viscometer using an "A" type spindle with a speed of 12 rpm), and a pH of 5.5.

What is claimed is:

1. Wet wipes comprising a wipe substrate and an emulsion composition, said emulsion composition being storage stable and having a delivered viscosity of no more than 500 mPas, said composition comprising water and
   a silicone based phase in the range of 1% to 20% by weight of said emulsion composition,
   a polymeric emulsifying composition in the range of 0.02% to 2% by weight of said emulsion composition,
   a stability composition, said stability composition comprising phenoxyethanol as a stability compound.

2. Wet wipes according to claim 1 wherein said phenoxyethanol is present in the range from 0.1% to 1% by weight of said emulsion composition.

3. Wet wipes according to claim 1 wherein said stability composition further comprises one or more stability compounds selected from sodium benzoate, potassium sorbate, methylparaben, propylparaben, ethylparaben, butylparaben, and disodium salt of ethylenediaminetetraacetic acid.

4. Wet wipes according to claim 3 wherein said sodium benzoate and/or said potassium sorbate are present in a combined quantity in the range of 0.1% to 1% by weight of said emulsion composition.

5. Wet wipes according to claim 1 wherein said stability composition is present in the range of 0.1% to 4% by weight of said emulsion composition.

6. Wet wipes according to claim 1 wherein said silicone based phase comprises one or more compounds selected from dimethicone, cyclomethicone and dimethiconol, dimethicone and trimethylsiloxysilicate, cetyl dimethicone, or combinations thereof.

7. Wet wipes according to claim 1 wherein said silicone based phase is present in the range of 2% to 10% by weight of said emulsion composition.

8. Wet wipes according to claim 1 wherein said emulsifying composition is a copolymer of C10–C30 alkyl acrylates and one or more monomers of acrylic acid, methylacrylic acid or one of their simple esters cross linked with an allyl ether of sucrose or an allyl ether of pentaerythritol.

9. Wet wipes according to claim 1 wherein said emulsifying composition is present in the range of 0.1% to 0.5% by weight of said emulsion composition.

10. Wet wipes according to claim 1 wherein said delivered viscosity is in the range of 100–300 mPas.

11. Wet wipes according to claim 10 wherein said delivered viscosity is in the range of 120 mPas to 180 mPas.

* * * * *